United States Patent [19]
Hall

[11] 4,416,663
[45] Nov. 22, 1983

[54] SELF-STERILIZING HYPODERMIC SYRINGE

[75] Inventor: Robert M. Hall, Capetown, South Africa

[73] Assignee: Steri-Pac, Inc., Pittsburgh, Pa.

[21] Appl. No.: 314,766

[22] Filed: Oct. 26, 1981

[51] Int. Cl.$^3$ .............................................. A61M 5/00
[52] U.S. Cl. .................................................... 604/163
[58] Field of Search ........... 128/218 R, 218 S, 218 N, 128/218 F, 215, 221, 220, 234; 604/171, 163, 158, 263, 264, 265, 267

[56] References Cited

U.S. PATENT DOCUMENTS

| | | | |
|---|---|---|---|
| 1,921,034 | 8/1933 | LaMarche | 128/218 F |
| 2,400,722 | 5/1946 | Swan | 128/215 X |
| 2,674,246 | 4/1954 | Bower | 128/215 |
| 3,134,380 | 5/1964 | Armao | 128/218 N X |
| 3,354,881 | 11/1967 | Bloch | 128/215 |

*Primary Examiner*—John D. Yasko
*Attorney, Agent, or Firm*—Carothers & Carothers

[57] ABSTRACT

A hypodermic syringe with a self-sterilizing needle, wherein a capsule containing sterilizing fluid and having perforative ends of flexible material with elastic memory tendencies for self sealing after axial penetration by the forward end of the needle is coaxially and slidably received over the forward end of the needle with the forward exposed end of the needle slidably penetrating one end of the capsule in perforation for sterilization of the needle. A guide is provided for the capsule, and guides the capsule for axial movement on the needle when axial force is applied against the outer end of the capsule, such as by engagement against the hide of an animal, to cause the exposed end of the needle to penetrate the outer end of the capsule for hypodermic penetration. A spring is also provided for axial urging and positioning the capsule outward to its original position of rest, such that the exposed end portion of the needle is again enclosed in the capsule for sterilization when the hypodermic penetration force is removed.

6 Claims, 4 Drawing Figures

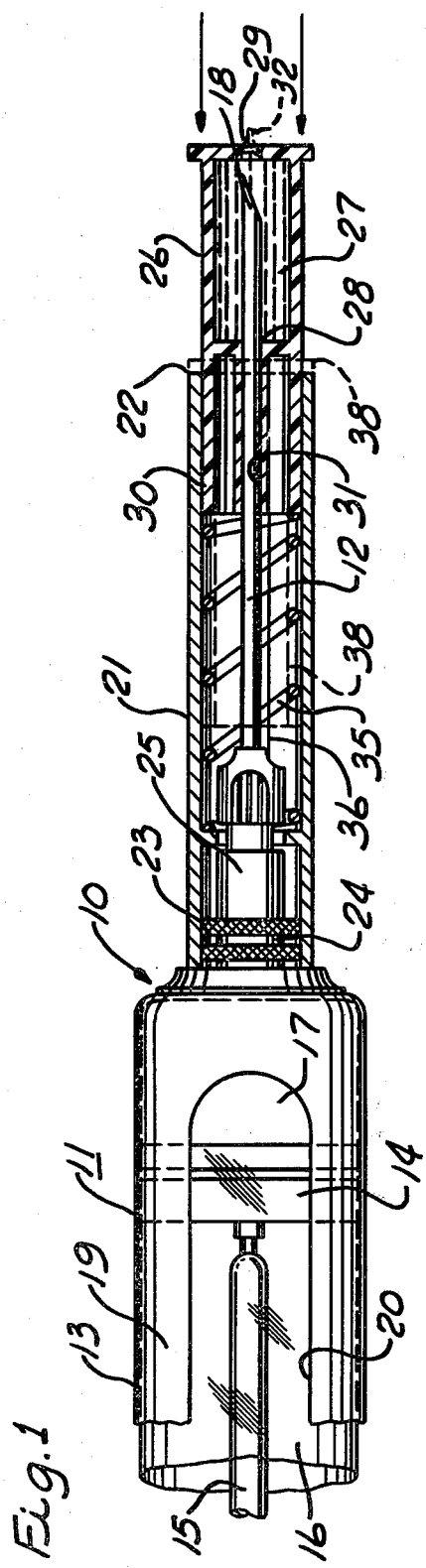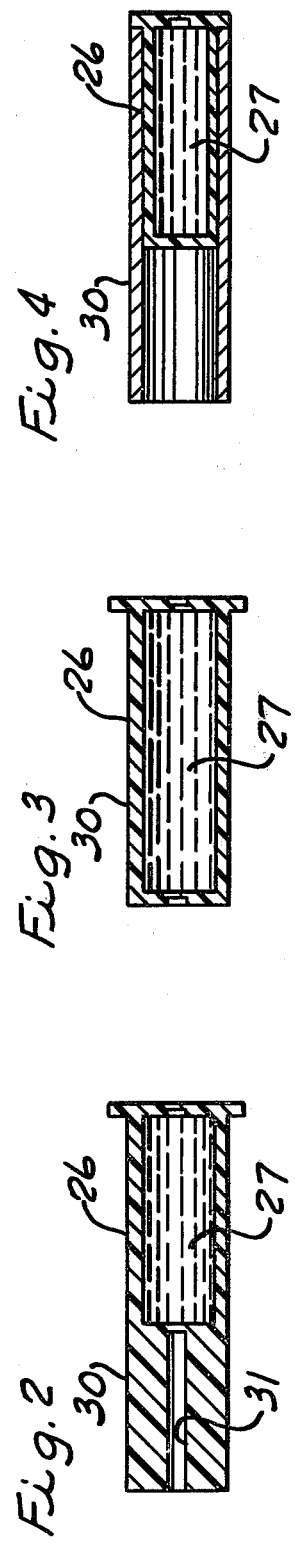

SELF-STERILIZING HYPODERMIC SYRINGE

BACKGROUND OF THE INVENTION

The present invention relates generally to hypodermic syringes, and more particularly for apparatus for sterilization of hypodermic syringe needles.

In veterinary medicine, large quantities of livestock, such as sheep, cattle or horses, have to be innoculated for the prevention of disease or for the cure of a disease through the use of a hypodermic syringe. During such innoculations, very unsanitary and dirty conditions are encountered out in the fields, and generally extensive sterilization standards which are cautiously followed when innoculating humans are not followed when innoculating livestock. Hundreds of livestock are innoculated at one period of time with the same hypodermic syringe in rapid succession. The needle generally is not sterilized between innoculations, and the result is that many infections are created simply as a result of the innoculation, a result of which is that some of the livestock is lost by death through the infection contracted through the innoculation.

The syringes utilized generally consist of a pistol-grip rubber or plastic plunger type syringe which meters out a predetermined quantity of innoculation serum with each actuation of the pistol-grip actuated plunger. Thus, one syringe is capable of holding a sufficient quantity of innoculation serum to innoculate a plurality of livestock. Due to this fact and further due to the fact that such large quantities of livestock have to be innoculated, it is not practical to replace the needle with a sterile needle after every innoculation, or to sterilize the needle between innoculations.

It is a principal object of the present invention to eliminate these foregoing problems and to provide a hypodermic syringe which automatically sterilizes the same needle after each innoculation while still permitting rapid successive uses of the same syringe.

SUMMARY OF THE INVENTION

The self-sterilizing hypodermic syringe of the present invention is provided for repeated use in veterinary applications or the like and generally comprises a hypodermic syringe including a tubular hypodermic needle fitted at one end with fluid pressure means to eject or draw fluid through the hypodermic needle together with means to automatically self sterilize the needle after each application. The means for sterilization comprises a capsule containing sterilizing fluid or gel and having perforative ends of flexible material with elastic memory tendencies for self sealing after axial penetration by the forward end of the needle, which is coaxially and slidably received over the forward end of the needle such that it slidably penetrates one end of the capsule in perforation and is thus lodged in the sterilizing fluid for sterilization. A capsule guide slidably guides the capsule for axial movement on the needle when axial force is applied against the other outer end of the capsule, such as by forcing the syringe and the outer end of the capsule against an animal hide for hypodermic penetration, to cause the exposed forward end of the needle to penetrate out through the other outer end of the capsule for hypodermic penetration.

After hypodermic penetration has been accomplished, and the required amount of innoculation serum has been injected into the animal, the syringe is retracted and spring means axially urges the capsule outward and repositions it to its original position of rest, such that the exposed end portion of the needle is again enclosed within the capsule for sterilization. The perforation made by the needle in the outer end of the capsule self seals, and the syringe is again ready for an immediate innoculation of the next animal.

The slide guide which slidably guides the capsule within the tubular guide may take on different configurations. In one embodiment, this capsule guide means may consist of the body of the sterilization capsule itself, or a body extension thereof, which is slidably received coaxially in a tubular guide, coaxially received over the needle with clearance, with the needle axially penetrating the capsule during use.

In another embodiment, the capsule guide means may consist of a capsule guide sleeve which is coaxially and slidably received in the tubular guide with the sterilization capsule coaxially and removably received in the forward end of this guide sleeve.

In yet another configuration, the capsule guide means may consist of an integral body extension of the capsule at one end thereof which is also provided with an axial guide bore aligned with the inner perforative end of the capsule to receive and guide the forward end of the needle for initial penetration or perforation of the inner or one end of the capsule, and to thereafter slidably guide the capsule for axial movement on the needle. In this embodiment, no tubular guide as previously described is required.

The spring utilized to reposition the capsule for sterilization of the forward end of the needle after innoculation may consist of a coiled compression spring and may further be provided with a flexible line, or other means, of predetermined length that is secured at its opposite ends to the opposite ends of the spring to limit the possible length of extension of the compression spring. This prevents the compression spring from dislodging the capsule completely off the end of the exposed forward end of the needle and assures proper positioning of the capsule for sterilization of the needle.

BRIEF DESCRIPTION OF THE DRAWINGS

Other objects and advantages appear in the following description and claims.

The accompanying drawings show, for the purpose of exemplification without limiting the invention or the claims thereto, certain practical embodiments illustrating the principles of this invention wherein:

FIG. 1 is a view in side elevation of the self-sterilizing hypodermic syringe of the present invention with portions of the syringe plunger body removed and with the forward self-sterilizing section of the syringe shown in vertical cross section for internal viewing.

FIG. 2 is a view in vertical cross section of another sterilizing capsule utilized in the syringe illustrated in FIG. 1 with modifications.

FIG. 3 is a view in vertical cross section illustrating yet another embodiment of the capsule illustrated in FIG. 2.

FIG. 4 is a view in vertical cross section illustrating a further embodiment of the sterilization capsules shown in FIGS. 1, 2 and 3.

DETAILED DESCRIPTION OF THE PREFERRED EMBODIMENTS

Referring to FIG. 1, the self-sterilizing hypodermic syringe 10 of the present invention is illustrated and in general is comprised of a conventional hypodermic syringe 11 that includes a tubular hypodermic needle 12 fitted at one end with fluid pressure means 13 to eject or draw fluid through hypodermic needle 12. Here, fluid pressure means 13 is illustrated as a conventional plunger syringe body which further consists of plunger or piston 14 which is axially actuated by piston rod 15 and is slidably received in glass barrel 16 to force innoculation serum contained within barrel 16 at the forward end thereof at location 17 in front of piston 14 to eject the serum through hollow or tubular hypodermic syringe needle 12. Plunger or piston 14 is actuated by a conventional pistol grip actuator (not shown) which is adjustable to vary the stroke of the pistol grip, and thereby limit the stroke of piston 14 to eject predetermined metered quantities of innoculation serum out through the forward end 18 of needle 12. Glass barrel 16 is housed and retained by outer metal housing 19 which is provided with windows 20 therein to permit viewing through glass barrel 16 to the interior. Syringe 11, which includes needle 12 and pistol grip plunger syringe body 13, are readily available on the market. One such syringe is sold under the trademark VACO by Ideal Instruments, Inc. of Chicago, Ill.

Referring next to the self-sterilizing improvements of the present invention, a tubular guide 21 is removably secured at its rearward end to syringe 11 with a portion 18 of the free forward end of needle 12 exposed beyond the other or outer end 22 of tubular guide 21 for hypodermic penetration. Tubular guide 21 is removably secured to syringe 11 by means of annular snap protrusions 23, which annularly fits or is received in annular groove 24 of needle adaptor 25 with a snap fit to rigidly hold tubular guide 21 in place coaxially about needle 12. Needle 12 is secured to needle adaptor 25 by a conventional rapid thread fitting.

Molded plastic capsule 26 contains sterilizing fluid or gel 27 which is sealed therein. This sterilizing fluid or gel may be of any conventional type of suitable sterilizing fluid. One such cold sterilizing gel is manufactured and sold by Union Carbide Corporation.

Capsule 26 is provided with a rearward perforative end 28 and a forward perforative end 29 of flexible material with elastic memory tendencies for self sealing after axial penetration by the forward end 18 of needle 12. In FIG. 1, capsule 26 is coaxially and slidably received over the forward end 18 of the needle with the forward disposed portion 18 of the needle slidably penetrating the capsule 26 in perforation such that it is lodged in the sterilizing fluid as illustrated. Capsule guide means in the form of tubular body extension 30 of capsule 26 is coaxially and slidably received in tubular guide 21, and thus slidably guides capsule 26 for axial movement in the tubular guide 21 when axial force is applied against the outer end of capsule 26 as indicated by the arrows to cause the exposed end 18 of needle 12 to penetrate the outer perforative end 29 of the capsule for hypodermic penetration.

The body extension capsule guide 30 is here illustrated as being integrally molded with capsule 26, and is in the form of a cylindrical rearward body extension of capsule 26 and is further provided with axial guide bore 31 which is aligned with perforative end 28 of capsule 26 to receive and guide the forward end 18 of needle 12 therethrough for needle perforation of end 28 of the capsule.

This permits one to initially and easily position the capsule by inserting the forward end 18 of needle 12 into the bore 31 and then to axially slide the capsule 26 rearward with force applied as indicated by the arrows to cause the sharp needle point to penetrate perforative end 28 to lodge the forward end 18 of needle 12 within the sterilizing fluid or gel 27 for sterilization thereof. The cylinder body guide 30 is coaxially received within tubular guide 21 and guides the axial sliding movement of capsule 26 to insure that the forward end 18 of needle 12 is axially aligned with the capsule at all times. When additional forces as indicated by the arrows are applied against the outer end of capsule 26, then capsule 26 will slide further down needle 12 in sliding engagement with tubular guide 21 and the forward pointed end 18 of needle 12 will puncture the perforative end 29 of capsule 26 and thereby expose the forward end 18 of the needle for hypodermic penetration of the needle into the animal's hide.

Due to the fact that the plastic of which capsule 26 is molded is a plastic material which has elastic memory tendencies, a good liquid seal will be maintained about the perforated end 28 of the capsule which is in sliding contact with the needle, and the same holds true when the forward end 18 of the needle perforates or penetrates through end 29 of the capsule. Even after the forward end 18 of needle 12 has penetrated perforative end 29 of the capsule, to punch or cut out a small segment of the flexible material as illustrated at 32 in dashed outline, and the capsule 26 is thereafter retracted in a direction opposite from the arrows illustrated to re-enclose the forward end 18 back within the sterilizing fluid 27, the small flap of material 32 will reclose the perforation at 29 to adequately seal the fluid 27 within the capsule during sterilization between innoculations.

Spring means in the form of coiled compression spring 35 is provided in tubular guide 21 for axially urging the capsule outward to position the capsule 26 at its original position of rest as illustrated in FIG. 1, such that the exposed end portion 18 of the needle is again enclosed within capsule 26 for sterilization when the forces applied against the outer end of capsule 26 as indicated by the arrows is removed. These forces are, of course, generally those applied when the outer end of capsule 26 is forced against the outside hide of an animal for hypodermic penetration of the exposed needle portion 18.

In order to insure that compression spring 35 will properly position or re-position capsule 26 to the sterilization position illustrated in FIG. 1 so that the exposed portion 18 of needle 12 is fully enclosed within the sterilizing fluid 27, a flexible line 36 of predetermined length has its opposite ends securely attached to opposite ends of the spring 35 to limit its length of extension as illustrated in the Figure. Thus, flexible line 36 assures that capsule 26 will not be fully ejected from tubular guide 21 due to the rapid axial expansion of spring 35 and further assures that capsule 26 will be positioned correctly as illustrated in FIG. 1 for sterilization of the needle end 18 even though the compressive values of spring 35 may change through wear.

To give an example of a typical operation or application of the self-sterilizing hypodermic syringe of the present invention, the needle 12 of proper length is secured to needle adaptor 25, then the plunger body 13 is filled in the area 17 in front of piston 14 with innoculation serum or the like in a conventional manner. Tubular guide 21 is then snapped into position coaxially over needle 12 with a snap fit as indicated at 23. Tubular guide 21 already contains compression spring 35 with its attached limit line 36. Then the plastic capsule 26 with sterilizing fluid or gel 27 therein is placed in position by sliding the forward end 18 of needle 12 into the bore 31. When the forward point of needle 12 reaches perforative end 28, the outer end of the capsule is pushed as indicated by the arrows so that the needle point penetrates perforative end 28 and the capsule is coaxially slid rearward over needle 12 until the bottom thereof engages the top of compression spring 35. The exposed end 18 of needle 12 is now positioned within the fluid or gel 27 for sterilization.

Additional force is then applied against the outside end of capsule 12 as indicated by the arrows to cause the capsule 26 to slide further rearwardly against the compression forces of spring 35 to cause the point of needle 12 to piercingly penetrate perforative end 29 of capsule 26. This might be done in the first application by finger pressure of the operator, or these additional forces may be applied simply by pushing the outer end of capsule 26 against the hide of the animal to be penetrated.

In any event, the outer end of the capsule 26 is positioned against the hide of the animal, then the entire syringe is forced against the animal so that the forward sterilized end 18 of the needle 12 penetrates the hide of the animal, while at the same time causing capsule 26 to slide rearwardly against the forces of spring 35 to the full penetration depth such that the capsule is positioned as indicated by the dashed outline 38 under the compression of spring 35. At this point in time of hypodermic penetration, the injection is administered by operating piston 14, and thereafter the forward end 18 of needle 12 is withdrawn from the hide of the animal. At this time, the force being applied against the forward end of capsule 26 as indicated by the arrows is being removed and compression spring 35 accordingly forces the capsule 26 to slide outwardly to its original position of rest as illustrated in FIG. 1. Correct positioning is assured by the limit extension line 36. Thus, the forward end 18 of the needle 12 is retracted back into the interior of capsule 26 and the small perforation flap 32 adequately seals off the outer or forward capsule end to minimize leakage of the sterilizing fluid 27. From this discussion of the operation of the self-sterilizing hypodermic syringe of the present invention, it becomes obvious that every rapid successive injections may be administered while still insuring sterilization of the needle.

Referring next to FIG. 2, a slight modification of the capsule 26 is illustrated. Here the capsule is identical with the exception that the integral extension guide body 30 is molded as a solid unit instead of a hollow unit as illustrated in FIG. 1.

Referring next to FIG. 3, another modification of the capsule 26 is illustrated, wherein the capsule guide 30 is, in fact, an integral part of the capsule 26 itself, and in this instance, the needle guide bore 31 is not provided.

FIG. 4 illustrates yet another embodiment of the capsule 26, wherein the capsule guide 30 in this instance is provided in the form of an independent guide sleeve 30 which is slidably received within the bore of tubular guide 21 and capsule 26 is coaxially and removably received with a relatively snug fit in the forward end of guide sleeve 30. With this embodiment, the guide sleeve 30 may first be inserted within tubular guide 21 and then capsule 26 may be inserted in the forward end of guide sleeve 30 for axial penetration by the needle 12, or capsule 26 and sleeve 30 may first be assembled and then inserted as a unit into tubular guide 21.

In yet another more simplified embodiment of the present invention, the capsule 26 of either FIG. 1 or FIG. 2 is utilized in combination with spring 35 without tubular guide 21. Tubular guide 21 can be completely removed in this embodiment, and the capsule guide means is provided by the axial guide bore 31 of capsule body extension 30 alone, which slidably guides capsule 26 for axial movement on needle 12.

I claim:

1. A self-sterilizing hypodermic syringe for repeated use in veterinary applications or the like comprising, a hypodermic syringe including a tubular hypodermic needle fitted at one end with fluid pressure means to eject or draw fluid through said hypodermic needle, the improvement comprising a capsule containing sterilizing fluid and having perforative ends of flexible material with elastic memory tendencies for self sealing after axial perforation by the forward end of said needle, said capsule coaxially and slidably received over the forward end of said needle with the forward exposed portion of said needle slidably penetrating one end of said capsule in perforation and lodged in said sterilizing fluid, capsule guide means slidably guiding said capsule for axial movement on said needle when axial force is applied against the other end of said capsule to cause said exposed end of said needle to penetrate said other outer end of said capsule for hypodermic penetration, said capsule guide means including a rigid tubular guide sleeve coaxially received over said hypodermic needle with clearance, one end of said tubular guide sleeve removably secured to said syringe with a portion of the free forward end of said needle exposed beyond the other end of said tubular guide sleeve for hypodermic penetration, said capsule slidably receivable in said tubular guide sleeve for guided axial movement, and spring means for axially urging and positioning said capsule outward to its original position of rest, such that said exposed end portion of said needle is again enclosed in said capsule for sterilization when said force is removed.

2. The self-sterilizing hypodermic syringe of claim 1, wherein said capsule guide means further includes an integral body extension of said capsule at said one end which is slidably received in said tubular guide sleeve.

3. The self-sterilizing hypodermic syringe of claim 1, wherein said capsule guide means further includes an integral body extension of said capsule at said one end which is slidably received in said tubular guide sleeve.

4. The self-sterilizing hypodermic syringe of claim 1, wherein said body extension includes an axial guide bore aligned with said one perforative end of said capsule to receive and guide the forward end of said needle for perforation of said one end of said capsule.

5. The self-sterilizing hypodermic syringe of claim 1, wherein said capsule guide sleeve means further includes a guide sleeve coaxially and slidably received in said tubular guide, said capsule coaxially and removably received in the forward end of said guide sleeve.

6. The self-sterilizing hypodermic syringe of claim 1, wherein said spring means consists of a coiled compression spring with limit means to limit the length of extension of said spring to a predetermined maximum.

* * * * *